United States Patent [19]

Tsukida

[11] Patent Number: 4,939,940
[45] Date of Patent: Jul. 10, 1990

[54] POST-ACCIDENT SAMPLE STATION NEEDLE SEAL

[75] Inventor: Robert S. Tsukida, San Jose, Calif.
[73] Assignee: General Electric Company, San Jose, Calif.
[21] Appl. No.: 296,993
[22] Filed: Jan. 17, 1989
[51] Int. Cl.$^5$ .............................................. G01N 1/20
[52] U.S. Cl. ............................. 73/864.74; 73/864.01; 141/329; 422/103
[58] Field of Search ................ 73/863, 864.01, 864.14, 73/864.51, 864.74, 864.85, 864.86, 864.87, 864.91; 422/103; 141/329, 330

[56] References Cited

U.S. PATENT DOCUMENTS

| | | | |
|---|---|---|---|
| 2,946,486 | 7/1960 | Gilmont | 73/864.14 X |
| 3,868,854 | 3/1975 | Travor et al. | 73/864.74 |
| 4,041,994 | 8/1977 | Horwitz et al. | 141/329 X |
| 4,153,076 | 5/1979 | McNeil et al. | 137/635 X |
| 4,267,451 | 5/1981 | Berick | 250/367 X |
| 4,311,484 | 1/1982 | Fusslien | 422/103 X |
| 4,558,603 | 12/1985 | Chlosta et al. | 73/864.85 X |
| 4,823,623 | 4/1989 | Carpenter et al. | 73/864.74 |

Primary Examiner—Tom Noland
Attorney, Agent, or Firm—Robert R. Schroeder

[57] ABSTRACT

In a post-accident sample needle system, at the sample station, an improved seal for a PASS liquid sample needle is disclosed. In such systems, a bottle with a septum is impaled on paired needles. The first needle provides venting, and the second needle provides for the placement of potentially radioactive samples in the bottle through the septum. A needle of the hypodermic type having an angled point is provided with a flared end remote from the point. A rubber O-ring fits over the needle adjacent the flare having an inner circumferential diameter that permits passage along the length of the needle and trapping at the end of the needle adjacent the flare. The O-ring is captured at the flared end of the needle by a conventional compression nut. The nut, when tightened, compresses the O-ring to circumferentially expand beyond the edges of the flare to form a seal between the needle and O-ring and to form a secondary seal between the bore and O-ring. In the expansion of the O-ring, the needle is self-centered and braced for the dispensing of a sample.

3 Claims, 3 Drawing Sheets

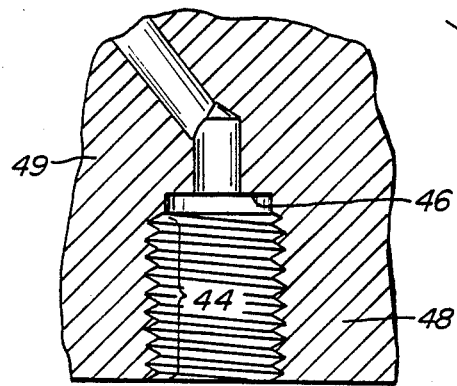
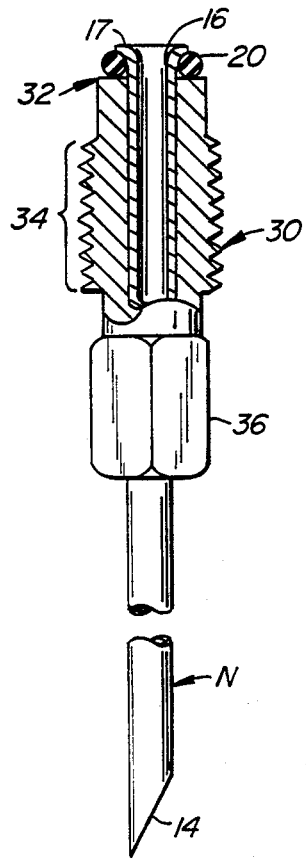
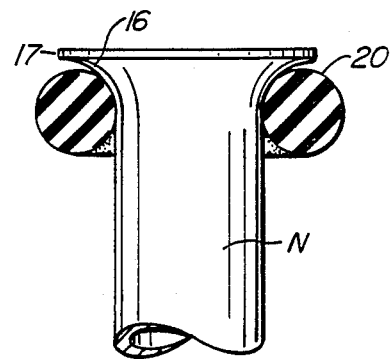
FIG._2A.
FIG._1.
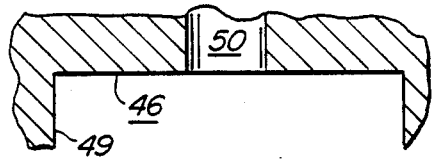
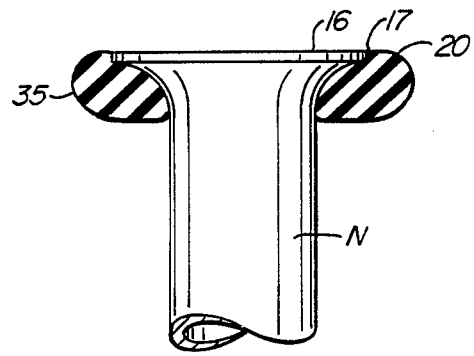
FIG._2B.

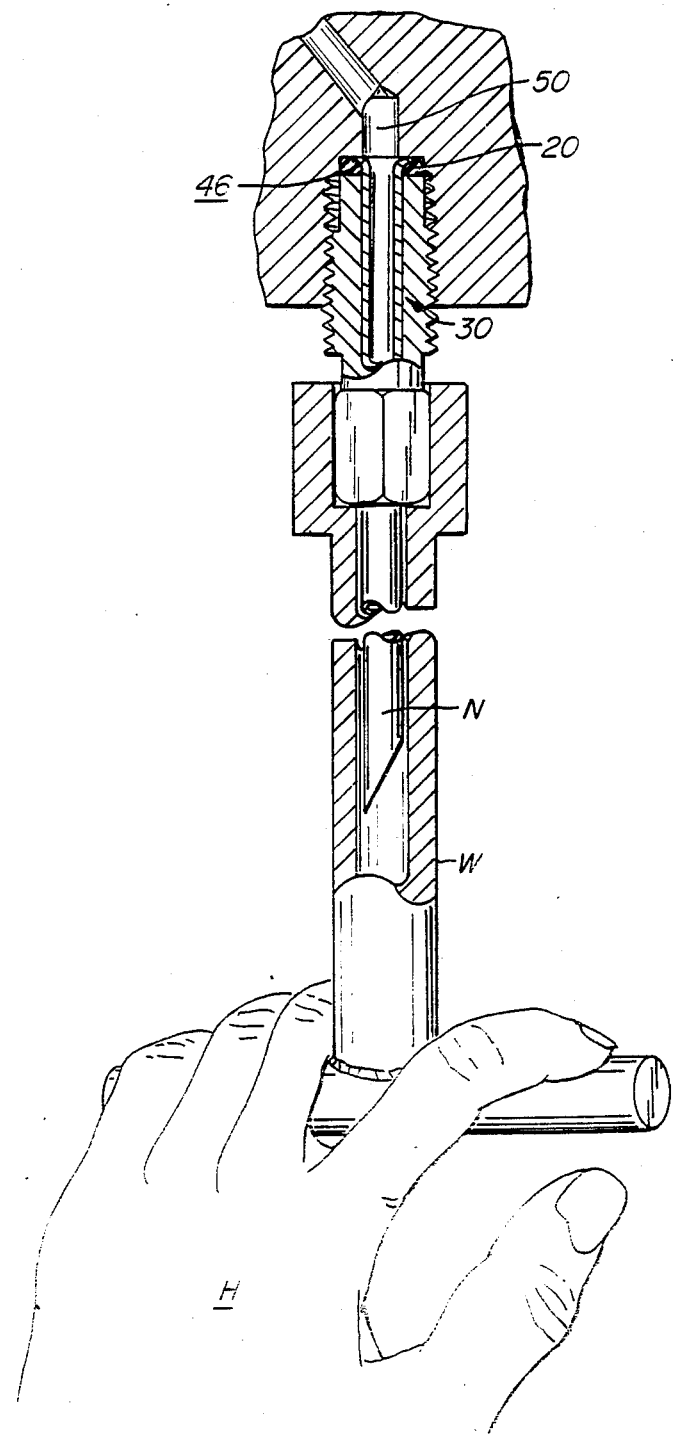
FIG_3.

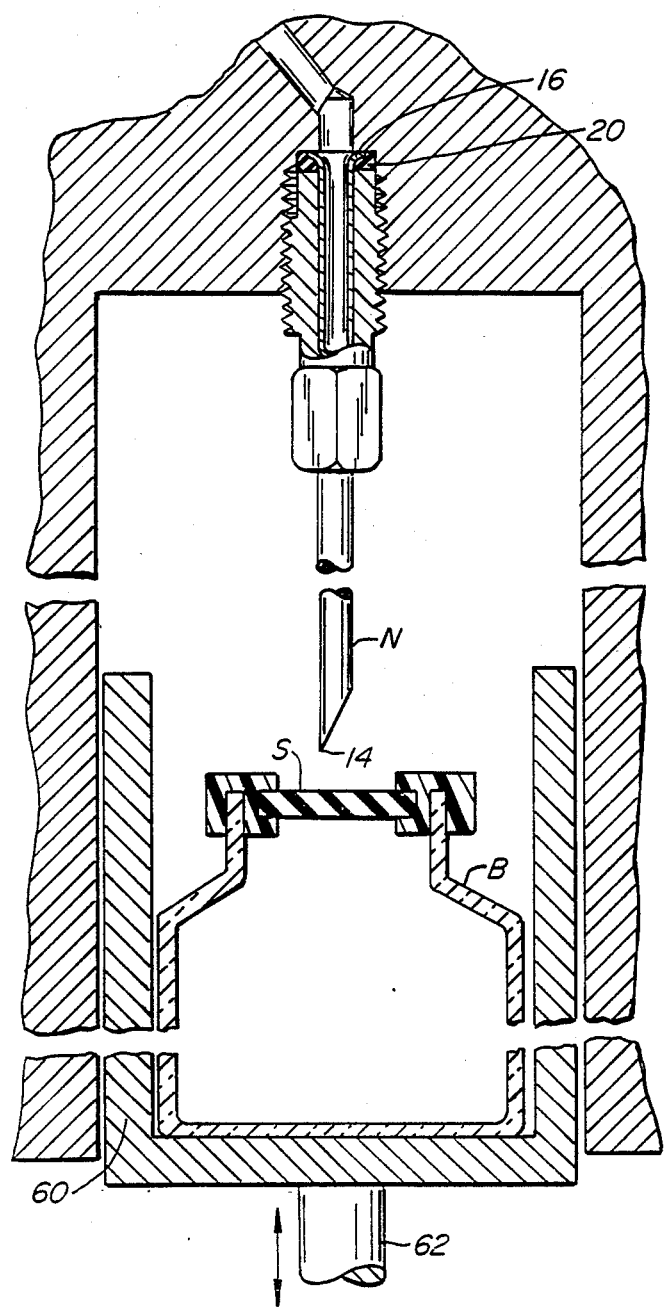
FIG._4.

POST-ACCIDENT SAMPLE STATION NEEDLE SEAL

BACKGROUND OF THE INVENTION

This invention relates to a post-accident sample system in a nuclear reactor. More particularly, at the post-accident sample station ("PASS"), an improved seal for a PASS liquid sample needle is disclosed for use in analyzing reactor samples following actual or suspected reactor casualties.

SUMMARY OF THE PRIOR ART

In prior art post-accident sample stations, an all metal needle has been used for affecting a seal. The reader will understand that post-accident sample systems channel radioactive waste to the post-accident sample station for deposit into sealed and shielded vials for analysis. It goes without saying that leaking of the radioactive materials is undesired.

Unfortunately, and heretofore, such needles have in fact leaked. This leaking can be traced to the all metal seals utilized to facilitate removal and reinstallation of needles in the prior art.

Simply stated, needles have heretofore been manufactured by having at their end a right angle annulus. The right angle annulus is registered to a complementary right angle surface in a bore for the mounting of the needle. A nut firmly presses the right angle metal of the seal against the end of the bore.

Leaks have occurred. Leakage paths have formed along the needle's outside surface between the needle's outside surface and the tightening nut utilized to hold the needle to the bore. Leaks have also formed along the outside surface of the tightening nut between the nut and the bore.

O-ring seals are known. O-ring seals have not been used in such assemblies because of the difficulty of their removal. When it is remembered that the wastes in the sample station, as well as the sample station itself, are radioactive, the complication which O-rings usually provide has militated against their use.

SUMMARY OF THE INVENTION

In a post-accident sample needle system, at the sample station, an improved seal for a PASS liquid sample needle is disclosed. In such systems, a bottle with a septum is impaled on paired needles. The first needle provides venting, and the second needle provides for the placement of potentially radioactive samples in the bottle through the septum. A needle of the hypodermic type having an angled point is provided with a flared end remote from the point. A rubber O-ring fits over the needle adjacent the flare having an inner circumferential diameter that permits passage along the length of the needle and trapping at the end of the needle adjacent the flare. The O-ring is captured at the flared end of the needle by a conventional compression nut. This compression nut has a blunt, cylindrical non-threaded end utilized to compress the O-ring. The nut further includes threads for screwing into a complementary threaded bore. Finally, the nut includes a typically hexagonal surface for engagement to a remote nut tightening or nut loosening wrench. When the needle is tightened into the bore by the nut, the O-ring is compressed. Upon such compression, the O-ring circumferentially expands to increase its outer diameter beyond the bounds of the flared end of the needle. The nut, when tightened, compresses the O-ring to self-circumferentially expand beyond the edges of the flare to form a seal between the needle and O-ring and to form a secondary seal between the bore and O-ring. In the expansion of the O-ring, the needle is self-centered and braced for the dispensing of a sample. The needle, at its flared end, and the O-ring, together with the nut, provide a convenient unit for installation and removal of the PASS sample needle from the post-accident sample station.

OTHER OBJECTS, FEATURES AND ADVANTAGES

An object of this invention is to use a needle with a flared end for installation at a post-accident sample station within a nuclear reactor. Specifically, the needle, at the end opposite its point, is flared. Typically, such a flared end of a needle presents an irregular surface. An O-ring is fitted over the pointed end of the needle and moved to and towards the flare at the opposite end of the needle. The needle and O-ring are then threaded through a retaining nut. The entire assembly, mounted to a remote socket tool, is then threaded to a bore for retaining the needle.

An advantage of the disclosed needle, O-ring and nut assembly is that the assembly is easy to install and easy to remove as a unitary assembly when attached to the end of a wrench for remote manipulation.

A further advantage of this assembly is that the O-ring is captured to the needle at the flare between the flare on one hand and the nut on the other hand. Consequently, installation of the O-ring to effect the seal and removal of the O-ring from a sealed disposition is facilitated by the flare at the end of the needle.

Yet another advantage is that the O-ring, as mounted to the end of the needle, typically has a diameter that is smaller than the bore. Consequently, the O-ring easily fits within the bore.

An additional advantage of the disclosed O-ring construction is that once the needle is tightened in place at the nut, the O-ring expands to form an improved seal.

First, the O-ring expands in circumference. It typically expands over the potentially serrated edges of the flared end of the needle. If these edges are jagged, the expanded O-ring is capable of effecting a leak-proof seal over these irregular surfaces.

Secondly, the O-ring seals fluid from passage along the wall of the needle.

Thirdly, the expanded O-ring seals the bore. No longer can radioactive fluid find its way past the O-ring along the sides of the nut to affect a leakage path.

Fourthly, the O-ring resiliently centers the needle in its sample station. This resilient centering enables the needle to receive successive columnar loadings each time a septum of a sample bottle is pierced. The successive columnar loadings do not affect, over a period of time, leakage.

BRIEF DESCRIPTION OF THE DRAWINGS

Other objects, features and advantages of this invention will become more apparent after referring to the following specification and attached drawings in which;

FIG. 1 is an exploded view of a flared needle having an O-ring captured by a nut adjacent the flare of the needle with the needle and nut assembly being presented to a bore at a post-accident sample station;

FIG. 2A is a section of the O-ring at the flared end of the needle, the O-ring being shown before compression to the bore;

FIG. 2B is a section similar to FIG. 2A with the O-ring shown compressed so as to expand its circumference, to effect a seal along the side wall of the needle, to effect a second seal at the side wall of the bore, and to provide a centered and resilient mount for the needle in the accident sample station;

FIG. 3 is a view of a remote socket being utilized for the installation and/or removal of the needle from the post-accident sample station; and, FIG. 4 is a perspective view illustrating the needle for the deposit of radioactive specimens in a shielded sample bottle, this view emphasizing the successive columnar loads that are placed upon the needle.

DETAILED DESCRIPTION OF A SPECIFIC EMBODIMENT

Referring to FIG. 1, a needle N is illustrated. The needle is typically a tube and has an angular cut 14 forming the needle point.

The needle extends to an opposite end 16. A flare is placed in end 16.

The reader will understand that when the needles are flared, the edge of the flare at 17 may become serrated with an irregular surface. Because of this serrated irregular surface, flaring of needles is not normally used where seals are desired.

An O-ring 20 is threaded over the needle. The O-ring 20 is threaded over the point end of the needle and captured at the flare 16.

Finally, a needle nut 30 is placed over the needle point 14 so as to capture O-ring 20 against the flare 16. Needle nut 30 has three component parts.

First, needle nut 30 has at a cylindrical end 32 a compression surface. As will hereinafter be demonstrated, surface 32 compresses the O-ring into the end of the bore into which the needle is to be received.

Secondly, needle nut includes male threads 34. Male threads 34 match complementary female threads 44 within a convention bore.

Finally, the needle nut includes a hex nut 36. Hex nut 36 functions as a male surface to cooperatively interact with the female surface of a wrench for the installation of the assembled needle assembly.

Having set forth the component parts of the needle assembly, the prior art bore can now be set forth.

Typically, the bore includes a lower sealing end 46. End 46 is typically fabricated by making a conventional drilled bore interior of a block of metal 48.

Once this bore is made, female threads 44 are tapped within the bore. It is to be noted that threads 44 do not penetrate all the way to the bottom of the bore 46. This enables a sealing ledge 49 to exist at the side walls of the bore some distance from the bottom of bore 46. It is into this ledge 49 that O-ring 20 is compressed once needle tightening occurs.

Having set forth the constituent parts with respect to FIG. 1, the installation and tightening interaction of the O-ring and flared needle end can be understood by the respective use of FIGS. 2A and 2B.

Referring to FIG. 2A, it can be seen that needle N at flare 16 has a diameter substantially less than the bore 46. Furthermore, and more importantly, it can also be seen that O-ring 20 has a diameter smaller than the bore. This enables the needle at the O-ring to fit firmly within the bore without interference with the side walls during insertion. Likewise, and during removal, the O-ring is removable from the bore.

Referring to FIG. 2B, the sealing and self-centering action of the needle at the flare by the O-ring can be understood.

First, it will be seen that the O-ring circumferentially expands. It expands from a diameter wherein the O-ring passed interiorly of the bore 49 without interference to a new diameter. This new diameter expands the O-ring in the circumferential dimension. Specifically, it effects a seal with the side of the bore generally in the area 35 of the O-ring 20. Consequently, a leak path from a radioactive waste flowing into the bore 46 from the post-sample accident system cannot find its way along the side edges of the bore 46 at 49 and thence to an uncontrolled leak.

Secondly, it will be seen that the O-ring, as expanded to its increased circumferential diameter, has passed over and beyond the edges of the flare 16. Specifically, it has conformed itself around any serrated edge at 17. In such conformance, an additional seal has been effected. This seal has been effected at the bottom or base of the bore along the base surface 46.

It will be understood that a flared and irregular end on the edge of a needle would not normally be used to effect a seal. Here, however, with the conformance of the O-ring over any serrated edge 17 of the flare 16, a seal nonetheless is effected.

It will be further understood that the needle N is subject to columnar loads. It has been found that the flared construction 16 with the disclosed self-centering and double sealing O-ring 20 in the compressed disposition illustrated in FIG. 2B is particularly effective to handle intermittent loadings.

Referring to FIG. 3, a socket wrench W is shown being tightened by the hand H of a worker at the nut. It can be seen that the entire needle assembly, including the needle N, the O-ring 20 and the nut assembly 30 are all movable as a unit into the bore 46 to affect the seal of the radioactive fluid dispensing conduit 50. It will be understood that the remote installation herein disclosed effects the seal.

FIG. 4 is for the understanding of the reader so that the repeated columnar impacts to which this needle assembly is subjected can be understood.

Typically, a sample bottle B having a conventionally-mounted septum S is placed within shielding 60 and remotely actuated via a shaft 62 into impalement on the needle N. In such impalement, dependent upon the sharpness of the needle N at point 14, successive columnar loads are placed at the flared end 16 of the needle and the trapped O-ring 20. These successive columnar loads are resiliently absorbed by the material of the O-ring 20 all the while the seal is maintained. Additionally, any cracks forming in the flared end due to the successive loads are automatically sealed, and leakage paths will not be formed as a result of the crack.

What is claimed is:

1. A needle assembly for sealing to a bore, the bore including a bottom surface; a passageway penetrating centrally of the bottom surface; a smooth cylindrical bottom extending from the bottom surface part way to and towards the opening of the bore; and female threads for receiving a needle retaining nut at complementary male threads, the improved needle assembly comprising;

a needle having a point at one end and an outward flare at the opposite end;

a resilient O-ring threaded over the end of said needle and captured at the flare of said needle at the end of said needle opposite said point;

a needle nut having a compression portion, a male threaded portion for mating to the female threads of said bore, and a socket portion for enabling securing of said needle interior of said bore;

said O-ring dimensioned with respect to said flare to fit interiorly of said bore without interference of the side walls thereof;

said O-ring having sufficient resiliency to expand in circumferential diameter beyond the edges of said flare for effecting a first seal between said flared needle end and said O-ring and effecting a second seal between said bore and said O-ring;

said O-ring effecting a self-centered seal for maintaining said seal under repeated, columnar impacts of said needle a respective septums for the deposit of radioactive sample in respective bottles without leaks.

2. The invention of claim 1 wherein said needle having said point at one end has the outward flare at the opposite end defining a potentially serrated edge.

3. A PASS sample needle for a post-accident sample station for impaling the septums of sample bottles and depositing a sample therein, the PASS sample needle comprising a bore having a flat bottom surface;

a passageway penetrating centrally of the flat bottom surface of said bore for supplying sample;

a smooth cylindrical bottom extending from the bottom surface of said bore part way to and towards the opening of said bore;

female threads defined in the side wall of said bore for receiving a needle retaining nut at complementary male threads;

a needle having a point at one end and an outward flare at the opposite end;

a resilient O-ring threaded over the end of said needle and captured at the flare of said needle at the end of said needle opposite said point;

a needle nut having a compression portion, a male threaded portion for mating to the female threads of said bore, and a socket portion for enabling securing of said needle interior of said bore;

said O-ring dimensioned with respect to said flare to fit interiorly of said bore without interference with the side walls thereof;

said O-ring having sufficient resiliency to expand in circumferential diameters upon the edges of said flare for effecting a first seal between said flared needle and in said O-ring and effecting a second seal between said bore and said O-ring;

said needle nut threaded to said bore to compress said O-ring, said O-ring is compressed effecting a self-centering seal for maintaining said seal under repeated columnar impacts of said needle at respective one of said septums of said sample bottles for the deposit of radioactive sample in said bottles without leaks.

* * * * *